United States Patent
Flores

(10) Patent No.: US 12,299,883 B2
(45) Date of Patent: May 13, 2025

(54) AUGMENTED INTELLIGENCE URINARY ANALYSIS

(71) Applicant: Josean Flores, Yauco, PR (US)

(72) Inventor: Josean Flores, Yauco, PR (US)

( * ) Notice: Subject to any disclaimer, the term of this patent is extended or adjusted under 35 U.S.C. 154(b) by 0 days.

(21) Appl. No.: 18/433,388

(22) Filed: Feb. 5, 2024

(65) Prior Publication Data
US 2024/0265528 A1 Aug. 8, 2024

Related U.S. Application Data

(60) Provisional application No. 63/443,379, filed on Feb. 4, 2023.

(51) Int. Cl.
| | |
|---|---|
| *G06T 7/00* | (2017.01) |
| *G01N 33/493* | (2006.01) |
| *G06T 7/12* | (2017.01) |
| *G06V 10/25* | (2022.01) |
| *G06V 10/764* | (2022.01) |
| *G16H 20/00* | (2018.01) |
| *G16H 50/20* | (2018.01) |

(52) U.S. Cl.
CPC ......... *G06T 7/0012* (2013.01); *G01N 33/493* (2013.01); *G06T 7/12* (2017.01); *G06V 10/25* (2022.01); *G06V 10/764* (2022.01); *G16H 20/00* (2018.01); *G16H 50/20* (2018.01); *G06T 2207/10056* (2013.01)

(58) Field of Classification Search
CPC ..................... G06T 7/0012; G06T 7/12; G06T 2207/10056; G01N 33/493; G06V 10/25; G06V 10/764; G06V 20/698; G16H 20/00; G16H 50/20; G16H 10/40; G16H 30/40; G16H 40/67
See application file for complete search history.

(56) References Cited

U.S. PATENT DOCUMENTS

| | | | |
|---|---|---|---|
| 2018/0322327 A1* | 11/2018 | Smith | G06V 20/698 |
| 2018/0330059 A1* | 11/2018 | Bates | G16H 10/60 |
| 2019/0385753 A1* | 12/2019 | Aganyan | G16H 15/00 |

* cited by examiner

*Primary Examiner* — Siamak Harandi
(74) *Attorney, Agent, or Firm* — Intellectual Property Consulting, LLC; Mark Melasky; Jared Rovira

(57) ABSTRACT

A computer-implemented method of performing, by a system of augmented intelligence, urinary analysis implemented on one or more processors and associated memory is provided. The method includes a first step of receiving an image of urine microscopy sample. The method includes a second step of detecting microscope light and a magnification technique. The method includes a third step of classifying said image according to the presence of urinary sediments by a machine learning model. The method includes a fourth step of identifying sediments in said image by said trained machine learning model if urinary sediments are present. The method includes a fifth step of classifying said urinary sediments by said trained machine learning model. The method includes a sixth step of generating a report of a presence or an absence of clinically significant urinary sediments in said urine microscopy sample.

19 Claims, 20 Drawing Sheets

AUGMENTED INTELLIGENCE URINARY ANALYSIS

CROSS-REFERENCE TO RELATED APPLICATIONS

This application claims priority to U.S. Provisional Patent Application Ser. No. 63/443,379, filed Feb. 4, 2023, the entirety of which is incorporated by reference as if fully disclosed herein.

BACKGROUND OF THE INVENTION

Field of the Invention

The present invention relates generally to using augmented intelligence to analyze urinary samples collected from patients for clinical diagnosis.

General Background

Microscopic examination of the urinary sediment is a tool of proven clinical utility. However, it requires training and expertise for proper identification of urinary casts. Incorrect cast identification my lead to flawed clinical decision making. Current limitations of urine sediment analysis include accessibility because specialized analysis may be available only at academic and research centers; time-consumption and delays because of processing, analysis, findings, and validation from specialists increase current workflow time and diagnosis requires timely decisions to be clinically relevant; sample processing requires specialized processing techniques and microscope settings are required correctly analyze samples; results can be interpreted incorrectly or incompletely because commercially available automated urine analyzers fail to identifying casts or acanthocytes. Accordingly, what is needed is a machine learning approach for automated real-time identification of urinary sediments.

SUMMARY OF THE INVENTION

In accordance with embodiments of the invention, a computer-implemented method of performing, by a system of augmented intelligence, urinary analysis implemented on one or more processors and associated memory is provided. The method includes a first step of receiving an image of urine microscopy sample of a patient. The method includes a second step of detecting of a microscope light and a magnification technique used to take said image. The method includes a third step of classifying said image according to the presence of urinary sediments by a trained machine learning model. The method includes a fourth step of identifying sediments in said image with bounding boxes by said trained machine learning model if urinary sediments are present in said image in the third step. The method includes a fifth step of classifying said urinary sediments within said bounding boxes by said trained machine learning model. The method includes a sixth step of generating a report of a presence or an absence of clinically significant urinary sediments in said urine microscopy sample from a predetermined list of clinically significant urinary sediments.

In accordance with embodiments of the invention, a computer-implemented method for operating one or more servers to provide a urinary analysis service is provided. The method includes a first step of detecting a request application executing on a computing device of a requestor, the request application automatically communicating with the service over a network. The method includes a second step of determining an availability of one or more available urinary analysis providers. The method includes a third step of providing data to the request application executing on the computing device to generate a presentation on a display of the computing device of the requestor, the presentation providing a user interface feature from which the requestor can trigger transmission of the service request to initiate, by the one or more servers, a selection process to assign the urinary analysis service request to one of the one or more providers. The service request received by a provider includes or is accompanied by at least an image of urine microscopy sample of a patient analyzed by a system of augmented intelligence. The said system of augmented intelligence comprises the steps of (i) receiving an image of urine microscopy sample of a patient, (ii) detecting a microscope light and a magnification technique used to take said image, (iii) classifying said image according to the presence of urinary sediments by a trained machine learning model, (iv) identifying sediments in said image with bounding boxes by said trained machine learning model if urinary sediments are present in said image in step (iii), (v) classifying said urinary sediments within said bounding boxes by said trained machine learning model, and (vi) generating a report of a presence or an absence of clinically significant urinary sediments in said urine microscopy sample from a predetermined list of clinically significant urinary sediments. The method includes a fifth step of in response to receiving the triggered transmission of the service request from the requestor interface feature, initiating the selection process by programmatically selecting an available provider from the one or more providers to be assigned to service for the requestor, and then providing information regarding the service request to the provider application executing on the computing device of the selected provider. The method includes a sixth step of upon the provider receiving the service request, the provider fulfills the service request, wherein said service request is fulfilled by the provider by reviewing said image of urine microscopy sample of said patient and verifying said report for accuracy.

In accordance with embodiments of the invention, a computer-implemented method for operating one or more servers to provide a urinary analysis service is provided. The method includes a first step of detecting a request application executing on a computing device of a requestor, the request application automatically communicating with the service over a network. The method includes a second step of determining an availability of one or more available urinary analysis providers. The method includes a third step of providing data to the request application executing on the computing device to generate a presentation on a display of the computing device of the requestor, the presentation providing a user interface feature from which the requestor can trigger transmission of the service request to initiate, by the one or more servers, a selection process to assign the urinary analysis service request to one of the one or more providers. The service request received by a provider includes or is accompanied by at least an image of urine microscopy sample of a patient analyzed by a system of augmented intelligence. The said system of augmented intelligence comprises the steps of (i) receiving an image of urine microscopy sample of a patient and (ii) identifying a presence or an absence of clinically significant urinary sediments in said urine microscopy sample. The method includes a fifth step of in response to receiving the triggered transmission of the service request from the requestor interface feature, initiating the selection process by programmatically selecting an available provider from the one or more providers to be assigned to service for the requestor, and then providing information regarding the service request to the provider application executing on the computing device of the selected provider. The method includes a sixth step of upon the provider receiving the service request, the provider fulfills the service request, wherein said service request is fulfilled by the provider by reviewing said image of urine microscopy sample of said patient and verifying said report for accuracy.

In accordance with embodiments of the invention, a computer-implemented method of performing, by a system of augmented intelligence urinary analysis implemented on one or more processors and associated memory, is provided. The method includes a first step of receiving an image of urine microscopy sample from a patient. The method includes a second step of detection of a microscope light and a magnification technique used to take the image. The method includes a third step of classifying the image according to the presence of urinary sediments by a trained machine learning model. The method includes a fourth step of identifying and classifying sediments in the image with bounding boxes by the trained machine learning model. The method includes a fifth step of classifying sediments within bounding boxes by the trained machine learning model. The method includes a sixth step of generating a report of presence or absence of significant sediments in the urine microscopy sample from a predetermined list of clinically significant urinary sediments.

BRIEF DESCRIPTION OF THE DRAWINGS

The foregoing and other objects, features, and advantages of the invention are apparent from the following detailed description taken in conjunction with the accompanying drawings in which like parts are given like reference numerals and, wherein.

Figure 1:
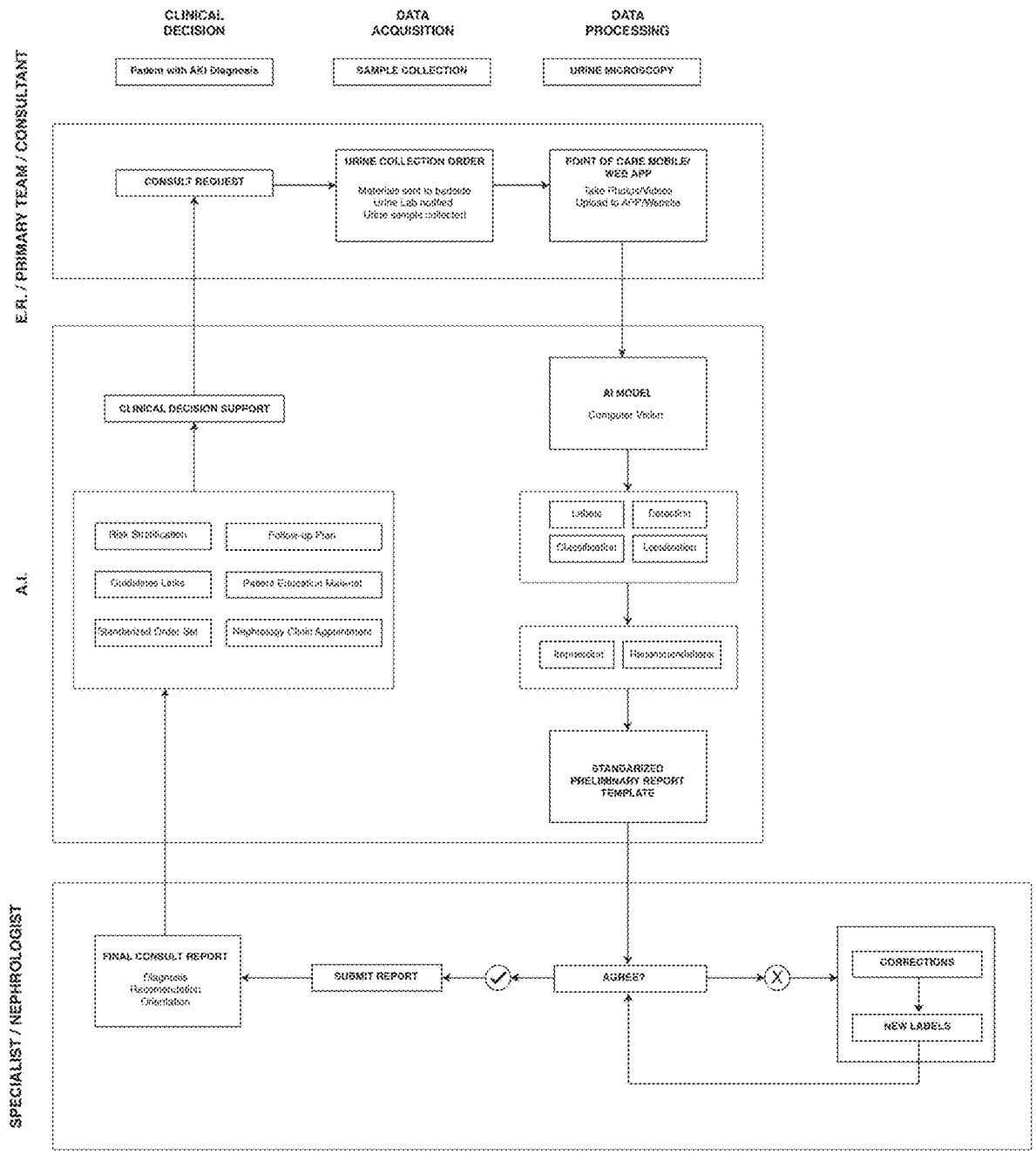
FIG. 1 depicts a flow chart of a Machine Learning Model urinary analysis in accordance with embodiments of the invention.

The images in the drawings are simplified for illustrative purposes and are not depicted to scale. Within the descriptions of the figures, similar elements are provided similar names and reference numerals as those of the previous figure(s). The specific numerals assigned to the elements are provided solely to aid in the description and are not meant to imply any limitations (structural or functional) on the invention.

The appended drawings illustrate exemplary configurations of the invention and, as such, should not be considered as limiting the scope of the invention that may admit to other equally effective configurations. It is contemplated that features of one configuration may be beneficially incorporated in other configurations without further recitation.

DETAILED DESCRIPTION

The embodiments of the disclosure will be best understood by reference to the drawings, wherein like parts are designated by like numerals throughout. It will be readily understood that the components, as generally described and illustrated in the Figures herein, could be arranged and designed in a wide variety of different configurations or be entirely separate. Thus, the following more detailed description of the embodiments of the system and method of the disclosure, as represented in the Figures is not intended to limit the scope of the disclosure, as claimed, but is merely representative of possible embodiments of the disclosure.

Microscopic examination of the urinary sediment is a tool proven clinical utility in multiple healthcare settings to guide the management of multiple high-risk conditions. Exemplary healthcare settings include outpatient clinics and hospitals and their departments such as emergency departments, intensive care units, and general wards. Exemplary high-risk conditions include Acute Kidney Injury (AKI), Acute Tubular Necrosis (ATN), Glomerulonephritis (GN), Acute Interstitial Nephritis (AIN), and Stones/crystal nephropathy. Embodiments of the invention are operable to use machine learning models to detect and identify urinary sediments automatically, assist physicians in the analysis of urinary sediments, facilitate documentation and communication of findings and recommendations, and provide specialized remote service to distant communities and resource-limited populations.

Figure 2:
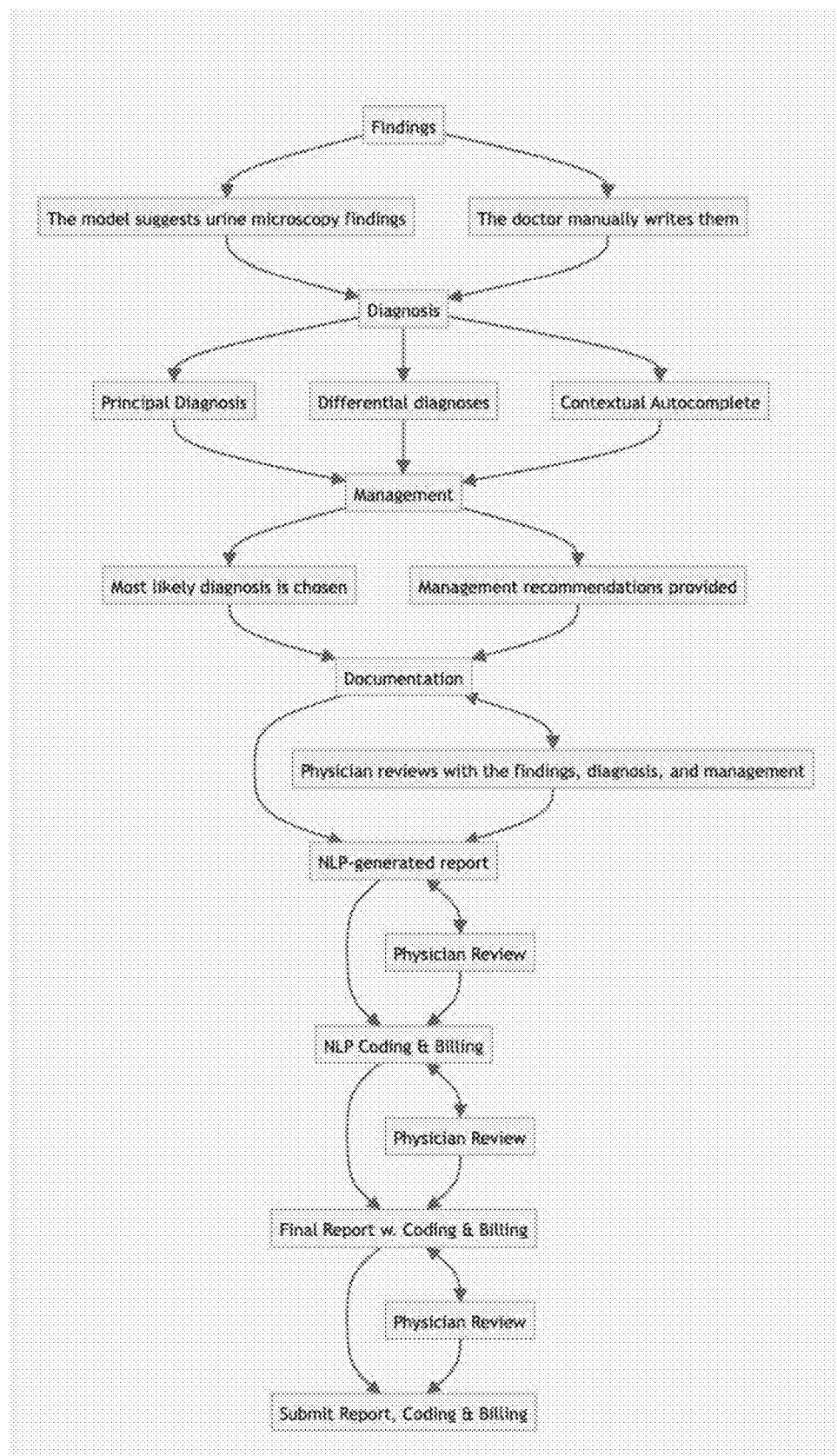
FIG. 2 depicts an improved physician workflow incorporating Machine Learning Model urinary analysis system and method in accordance with embodiments of the invention.

In accordance with embodiments of the invention, a computer-implemented method of performing, by a system of augmented intelligence urinary analysis implemented on one or more processors and associated memory, is provided, as illustrated in FIGS. 1 and 2, the method includes a first step of receiving an image of urinary microscopy sample from a patient. The method includes a second step of detection of a microscope light and a magnification technique used to take the image. The method includes a third step of classifying the image according to the presence of urinary sediments by a trained machine learning model. The method includes a fourth step of identifying and classifying sediments in the image with bounding boxes by the trained machine learning model. The method includes a fifth step of classifying sediments within bounding boxes by the trained machine learning model. The method includes a sixth step of generating a report of presence or absence of significant sediments in the urine microscopy sample from a predetermined list of clinically significant urinary sediments.

In some embodiments, the reports, images, labels and other model results are fed into a generative AI that produces a finalized, physician level report.

In one embodiment of the method, the sediments are casts or acanthocytes. Exemplary casts are muddy-brown granular casts showing acute tubular necrosis indicating severe acute kidney injury, granular casts showing acute tubular necrosis indicating moderate-severe acute kidney injury, and cellular cast showing interstitial nephritis or glomerulonephritis. In one embodiment, the sediments are acanthocytes indicating glomerulonephritis. In one embodiment, the sediments are crystals showing crystal-associated nephropathy indicating medication side effects and metabolic conditions.

Figure 3:
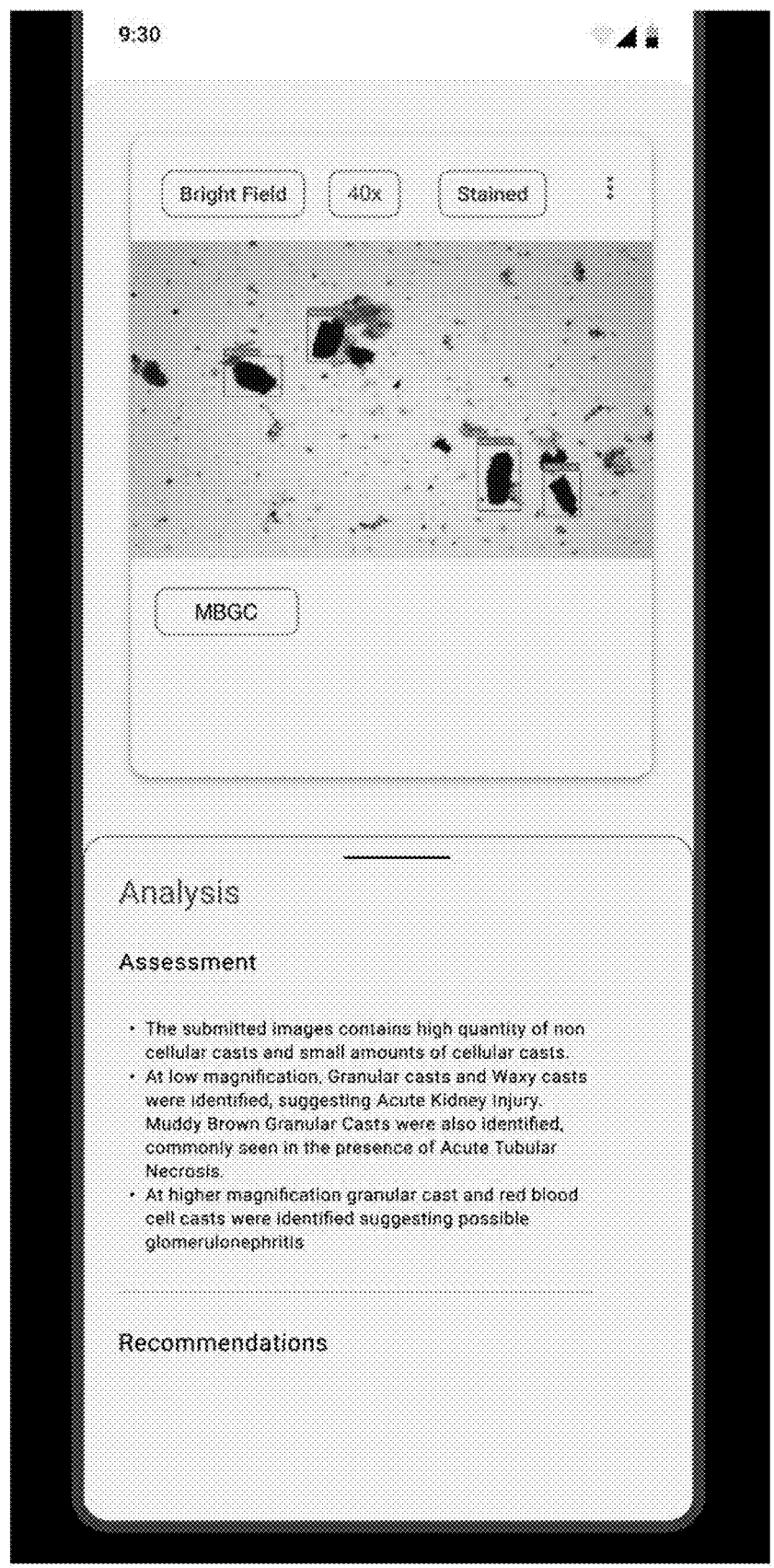
FIG. 3 depicts a mobile device displaying an example of a Machine Learning Model urinary analysis system generated report in accordance with embodiments of the invention.
Figure 4:
FIG. 4 depicts a mobile device displaying an example of an image of a sediment that has been identified and classified by Machine Learning Model urinary analysis system in accordance with embodiments of the invention.
Figure 5:
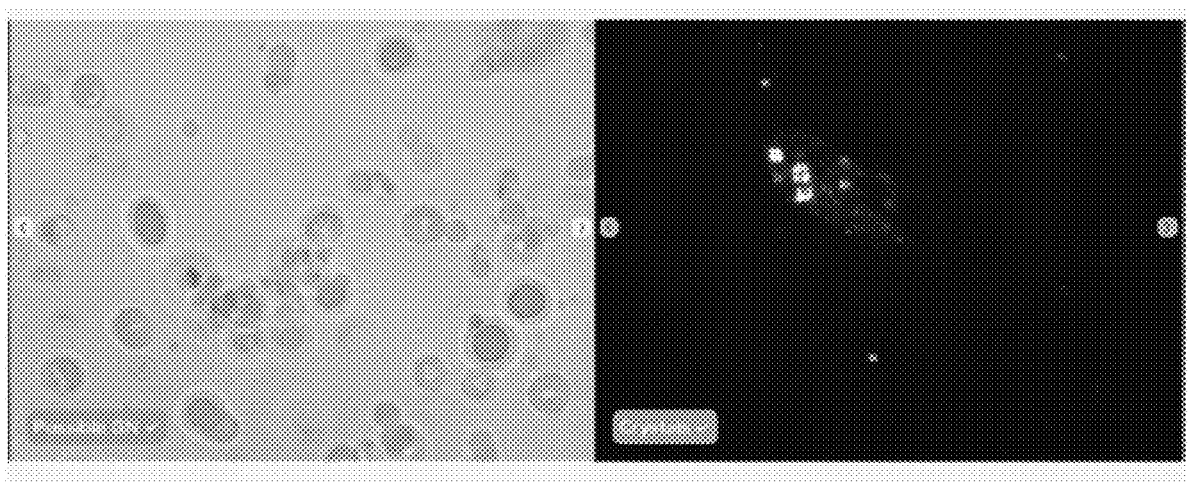
FIG. 5 depicts images taken using different magnification imaging techniques wherein the specific technique has been identified and labeled by Machine Learning Model urinary analysis system in accordance with embodiments of the invention.
Figure 6:
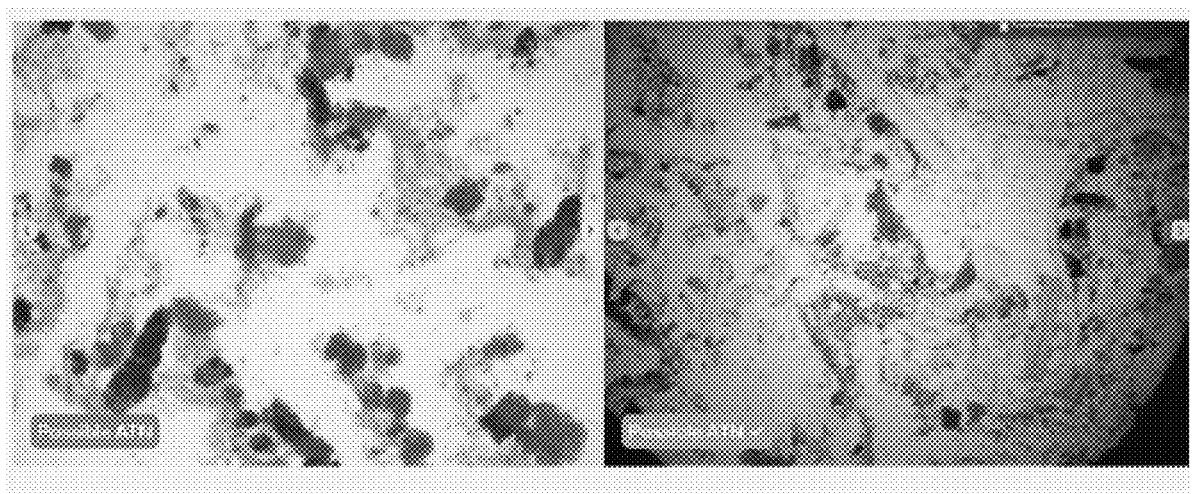
FIG. 6 depicts images taken using different magnification imaging techniques wherein the specific technique has been identified and labeled by Machine Learning Model urinary analysis system in accordance with embodiments of the invention.
Figure 7:
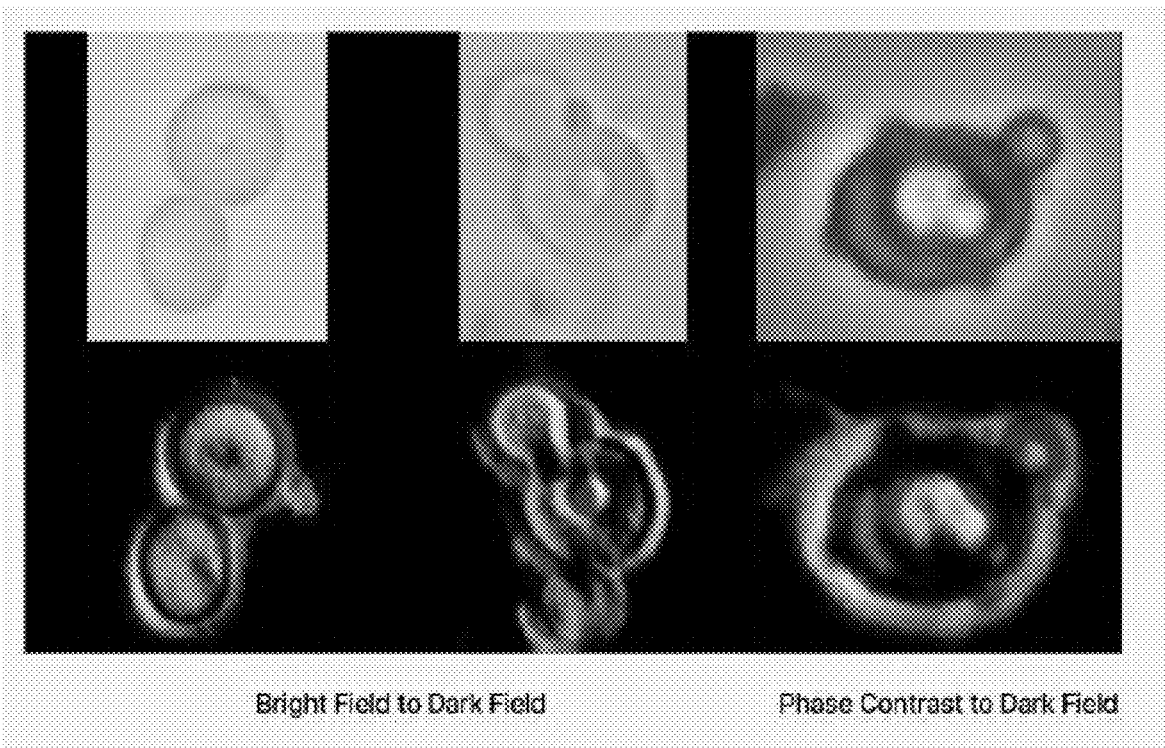
FIG. 7 depicts examples of images taken using different magnification imaging techniques.
Figure 8:
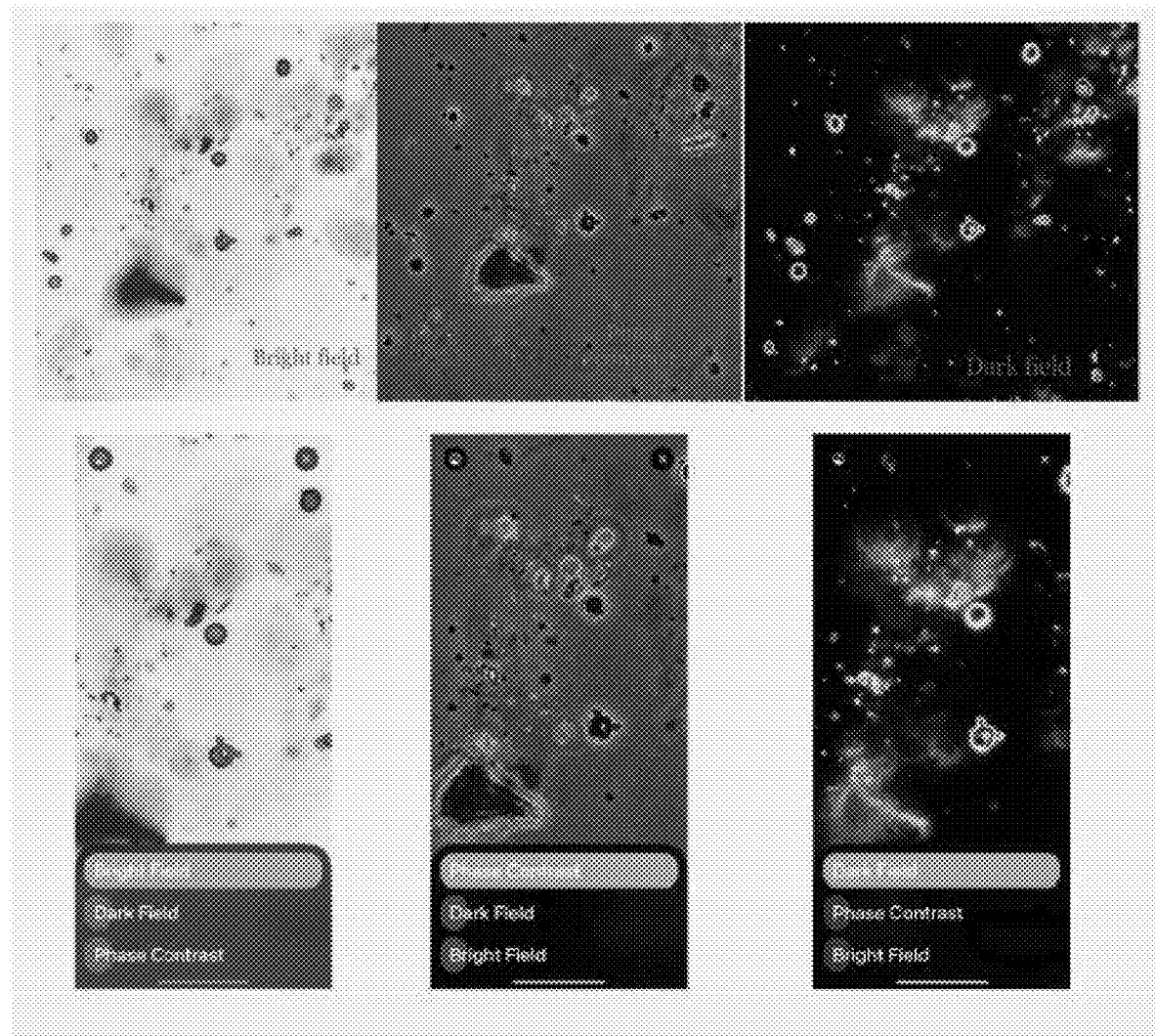
FIG. 8 depicts images taken using different magnification imaging techniques wherein the specific technique has been identified and labeled by Machine Learning Model urinary analysis system in accordance with embodiments of the invention.
Figure 14:
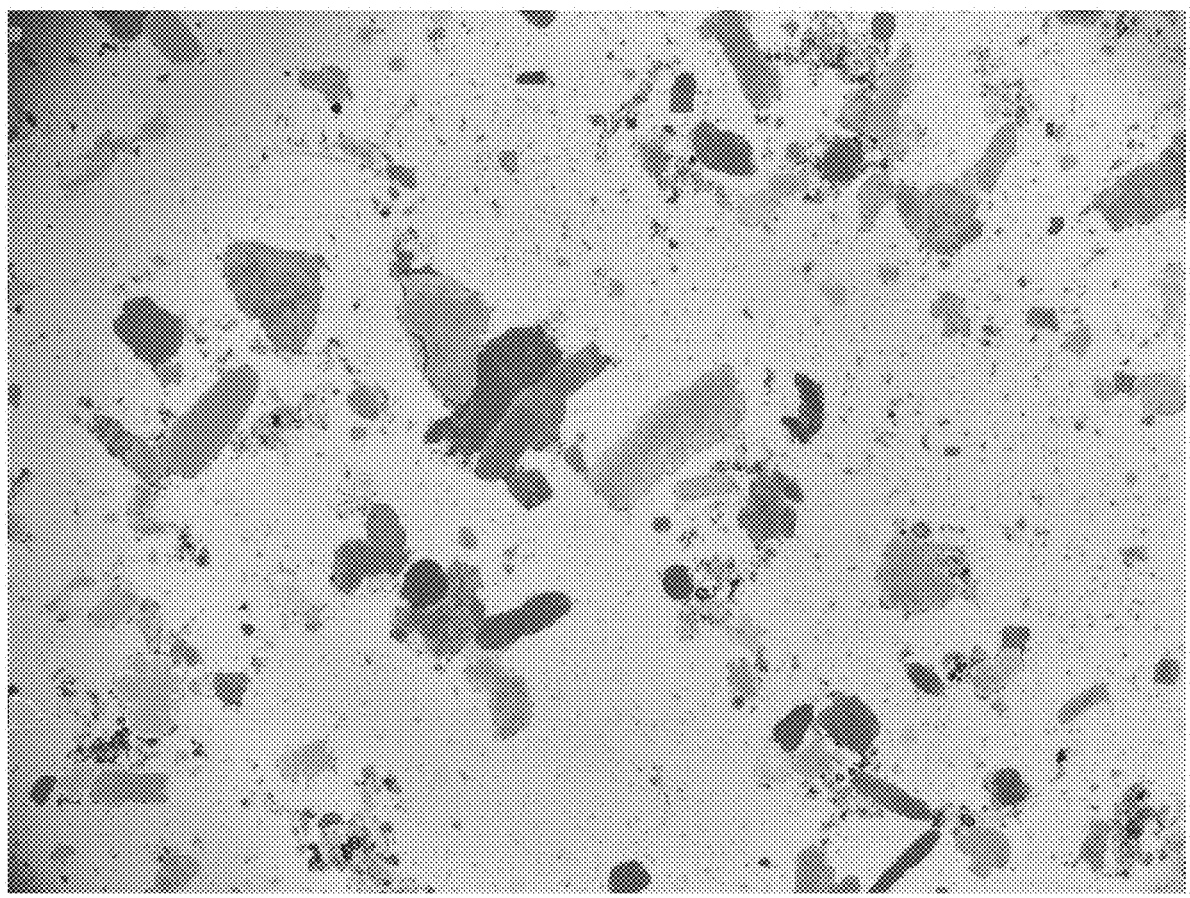
FIG. 14 depicts an example of an image before the Machine Learning Model urinary analysis system has performed analysis in accordance with embodiments of the invention.
Figure 15:
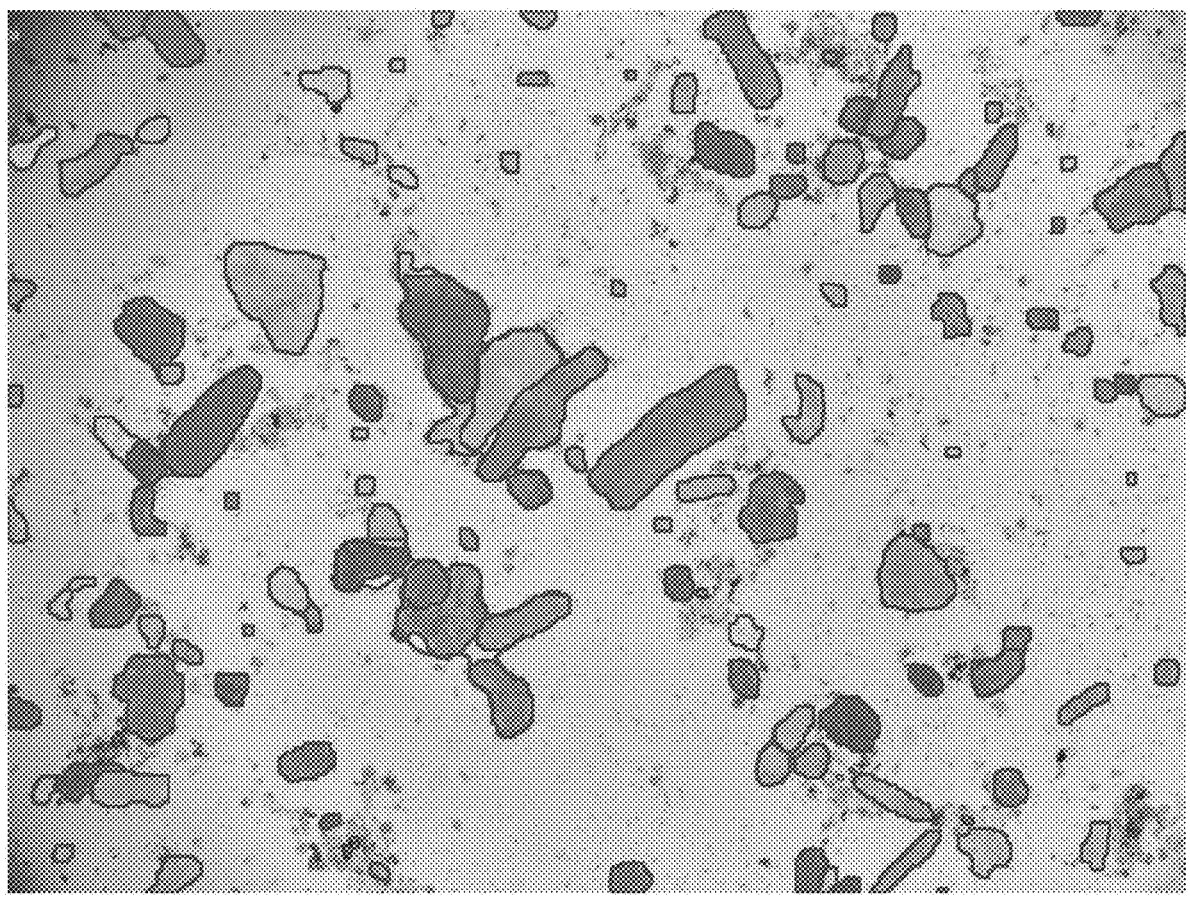
FIG. 15 depicts an example of an image after the Machine Learning Model urinary analysis system has performed an analysis and the sediments have been outlined in accordance with embodiments of the invention.

Embodiments of the invention are operable to automatically analyze a urine sample and create an autogenerated image analysis report that will include a summary of the findings, information about their clinical correlation, and initial management for a patient. See FIG. 3. The report may include data visualization of results, such as including images of the most significant findings and visualization of categorical and numerical data for further reference and interpretation. See FIG. 3-4. The report may include a containing an automatically generated analysis of the images. For example, the report may contain image classification, including (1) automatic detection of the microscope light and magnification technique used to take the image: bright field, dark filed, and phase contrast and ×10, ×40, ×60+; (See FIG. 5-8) (2) classifying the image according to the presence of urinary sediments, such as casts detected and acanthocytes detected; (3) classify the image based on the most likely possible diagnosis associated with image findings, such as acute tubular necrosis, acute interstitial nephritis, glomerulonephritis, and crystal nephropathy (See FIG. 9) and (4) sediment identification and classification such as localize sediments with bounding boxes and classify them under 3 types of casts or acanthocytes (See FIGS. 10-15). FIG. 14 illustrates an original image of a urinary sample before the Machine Learning Model urinary analysis system has performed an analysis in accordance with embodiments of the invention. FIG. 15 depicts an example of a urinary sample after the Machine Learning Model urinary analysis system has performed an analysis and the sediments have been outlined by segmentation masks in accordance with embodiments of the invention.

Embodiments of the methods are operable for interpretable machine learning. The machine learning model is operable to report the presence or absence of significant sediments from a predetermined list of clinically significant urinary sediments, along with the most frequently associated clinical diagnosis based on current medical literature (See FIG. 16). Based on the sediments, a report generated may contain management recommendations for its associated diagnosis which can be based on current practice guidelines. Management recommendations may focus on data gathering that could help to confirm or rule out the associated diagnosis. The method may also include important aspects of physical examination, diagnostic tests, laboratories, imaging studies, most likely complications, possible contraindicated medications, and initial treatment options for the diagnosis associated with the urinary sediment.

Embodiments of the invention are operable to provide clinical decision support. A method of such is outlined in FIG. 2. Physicians may use an unvalidated report or a validated report that has been reviewed by a specialist. This can be particularly useful in a remote or rural setting, where a nephrologist may not be available to review a urine sample. In that situation, a software app ecosystem may be utilized. A physician may order a urine sample and have that performed by a local lab. The lab will prepare a slide and generate an image under a microscope. As is usually the situation in any setting, the requesting physician does not have the ability to control the quality or methodology of the image taken by the lab. Embodiments of the method are operable to adjust for the differences in quality of the image as described above. Then the app will perform the steps of the method using the machine learning tools to identify sediments in the sample. The app will generate a report for the physician's use. The app may also be operable to remotely request a specialist to review a sample from a remote location. The physician may see results and desire a second opinion or confirmation. The system may have users with accounts configured to receive requests from treating physicians. The app may have an interface displaying the report and the images for a specialist to confirm remotely and make notes to confirm or send feedback regarding treatment or whether to take another sample, for example.

In an exemplary application of the method, Muddy Brown Granular Casts detected, indicating Possible Acute Tubular Necrosis. The method will generate a report directing physicians to consider assessing volume status and urine output. If output is decreased, consider a trial of IV diuretics and then limit IV fluids to prevent the risk of fluid overload.

In one embodiment, a machine learning model was created by accessing a database of microscopic examination of the urinary sediment images. Images were captured with a smartphone camera adapted to the microscope eyepiece. Images were categorized and labeled by trained observers and divided into datasets for classification and object detection tasks. Input contained annotations about illumination, staining, and magnification. Bounding boxes for 3 major structures: casts and acanthocytes were fed into the model. Preliminary experimentation was performed on a subset of images (308 images containing 691 casts and 573 acanthocytes) to train a YOLOv5 object detection model to identify acanthocytes and 3 types of clinically relevant urinary casts: muddy brown-granular, granular, and waxy casts. Images were preprocessed using YOLOv5 data augmentation technique. The model was trained with empty weights and on pre-trained models, with image sizes of 640 and 1280, batches of 5 and 14, and 300 epochs. Two models were trained; one for acanthocytes and casts, and another for acanthocytes only.

After model development and training, performance was validated in 113 additional images containing 472 acanthocytes and 172 casts. The best performance was obtained with YOLOv516 for acanthocytes only, with 1280 image size, a batch of 14, and 300 epochs. It achieved a mean average precision (mAP) of 0.0.955. Both models performed above benchmark datasets metrics. In this dataset, the different illumination techniques, degree of magnification, high-resolution images, and staining techniques served as different backgrounds that increased the model performance even with a small number of training data.

In an exemplary workflow, a primary team will request service of the platform, by an app, for example. A patient sample will be collected and processed at a clinical site. Images of the sample will be uploaded to the sample. The images will then be analyzed by computer vision models. Analysis results may be viewed and validated by a specialized physician. A validated report may be created and made available to the patient's primary care team accessible via the platform or through an electronic medical record software application interfacing with the platform.

Embodiments of the invention are operable to account for variation in microscopy images which may be received from samples collected in a lab. Quality of microscopes in labs may vary. Settings such as illumination (e.g., bright field, dark field, and phase contrast), light polarization, and magnification (e.g., ×10, ×20, ×40, and ×60) may affect images captured of urine samples. See FIGS. 5-8. Examples of variation of processing of samples, such as by a lab technician, include centrifuge RPM and time, supernatant handling, pellet resuspension, slide preparation, and staining. Urine samples may be collected in containers, syringes, or by Foley catheters in proximal or distal tube collections, for example. Variables affecting samples may include collection processing time and temperature after collection. With all the variables, physicians are expected to correctly detect the presence (or absence) of urine sediments, classify them, correlate clinically, document, and communicate in a timely manner, the management recommendations to primary team.

FIGS. 10-15 depict examples of an interface using bounding boxes overlayed on an image of a urine sample. The training a machine learning model is operable to display bounding boxes over sediments or foreign bodies it has identified as notable to the user. Classifying images by the presence or absence of sediments will help the physician quickly focus on images where there are sediments to be interpreted. Identifying sediments requires the use of different illumination techniques. Labeling the illumination technique used for each image will help the physician in the interpretation process and to quickly compare the same image under different illumination.

Many practices, clinics and hospitals, especially those in remote locations, are not equipped with microscopes and other equipment capable of the different illumination techniques required for proper sediment analysis, the current invention utilizes a trained model that can convert an image from one illumination technique to another. See FIGS. 5-8.

The model, when used in the analysis of higher magnification images, can interpret as the most probable class of sediment or other object among several classes and display the model's certainty of a given result. On lower magnification images, results can be presented as the percentage of each sediment present in the image.

Figure 9:
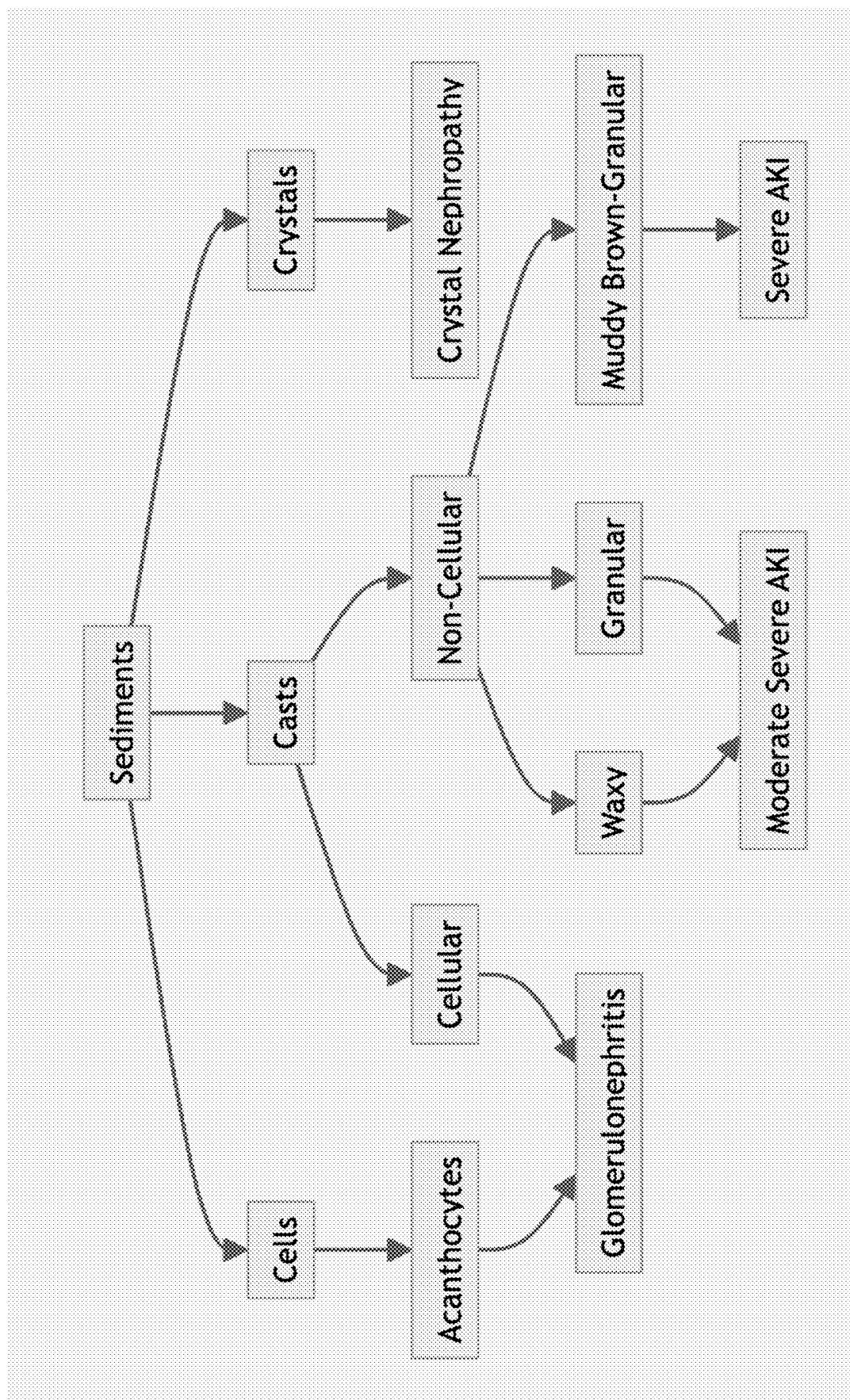
FIG. 9 depicts an example of simplified classification system used by the Machine Learning Model urinary analysis system in accordance with embodiments of the invention.
Figure 10:
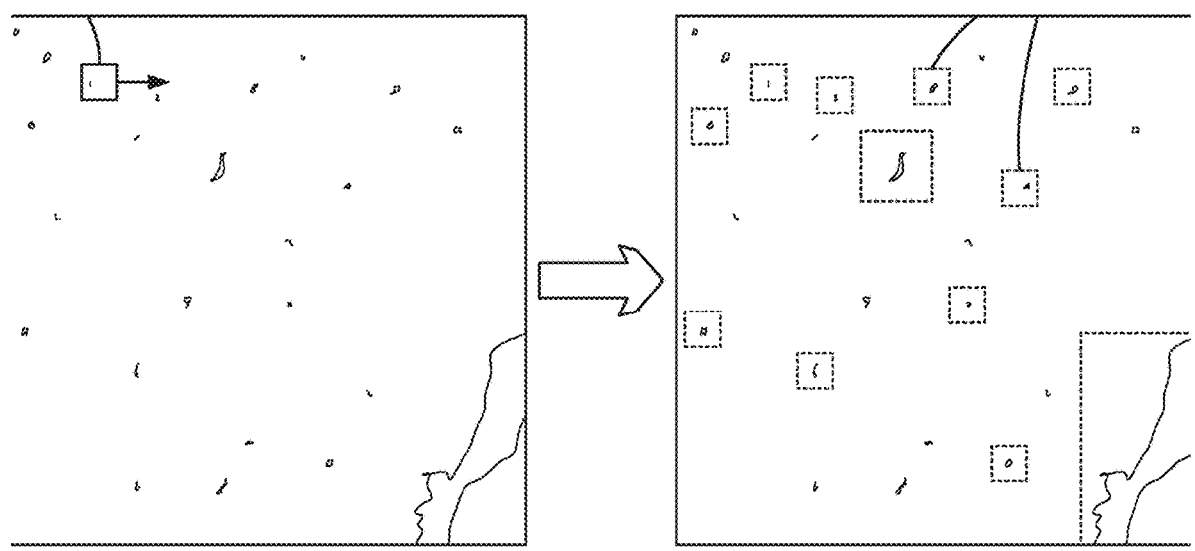
FIG. 10 depicts an example of an image analysis using bounding boxes by the Machine Learning Model urinary analysis system in accordance with embodiments of the invention.
Figure 11:
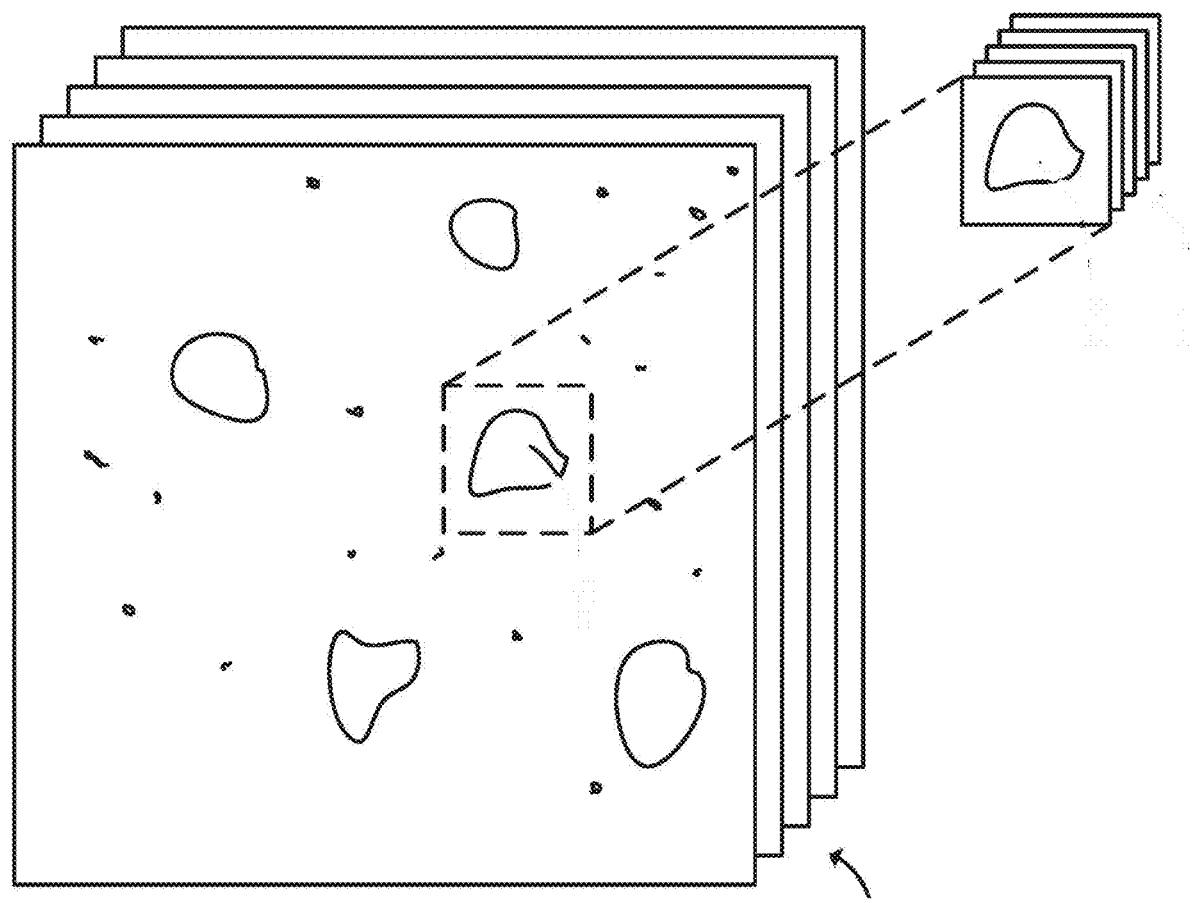
FIG. 11 depicts an example of an image analysis using bounding boxes by the Machine Learning Model urinary analysis system in accordance with embodiments of the invention.
Figure 12:
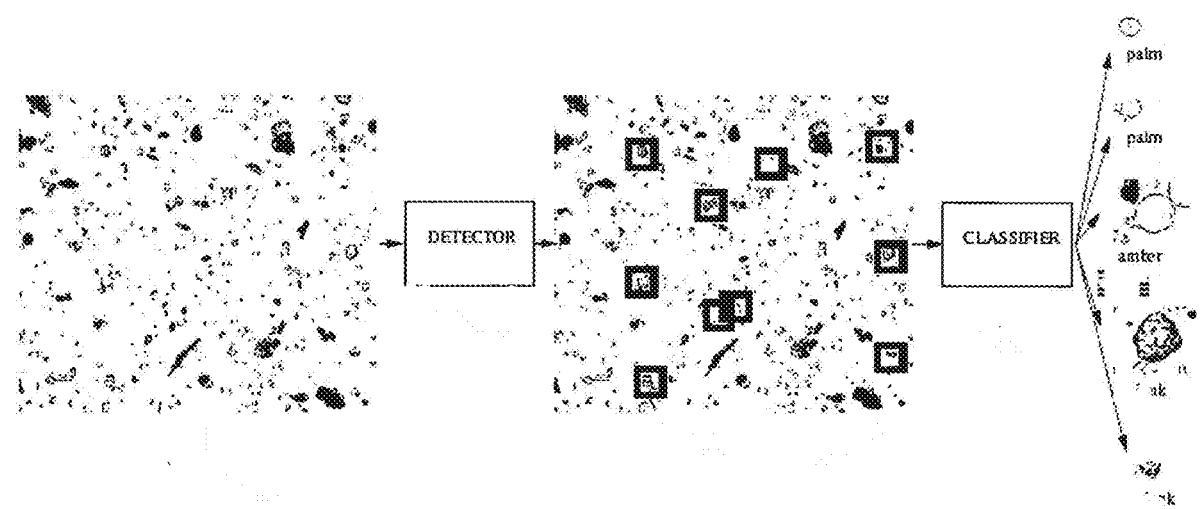
FIG. 12 depicts an example of an image analysis using bounding boxes by the Machine Learning Model urinary analysis system in accordance with embodiments of the invention.
Figure 13:
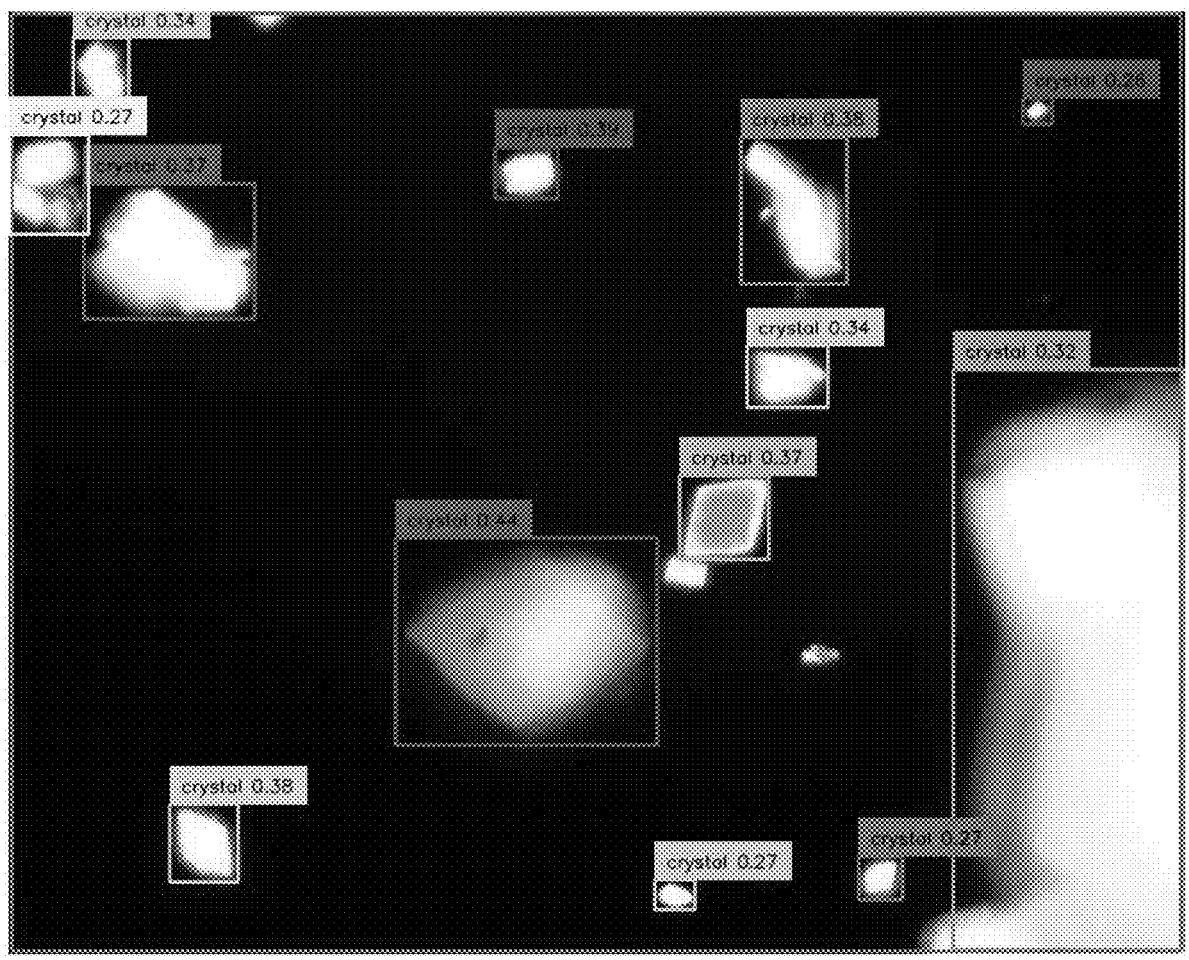
FIG. 13 depicts an example of an image analysis using bounding boxes by the Machine Learning Model urinary analysis system in accordance with embodiments of the invention.

Embodiments of the invention include a method of creating a urine sediment classifier model. FIG. 9 depicts a simplified example of a classification flowchart. In one embodiment, a classifier may be developed using image classification technique to classify the sediments. Images of urine samples are cropped to isolate sediments in the images. The original and cropped images are organized into folders according to their sediment class. An image classification model is trained using Apple CoreML software. The trained model is added to Apple's sample Xcode project and App. The classifier model may then be uploaded to a computing device for use identifying samples. However, one skilled in the art will appreciate that any machine learning software suite and method of training a model may be sufficient to train a model.

In accordance with embodiments of the invention, a computer-implemented method for operating one or more servers to provide a urinary analysis service is provided. An advantage of this embodiment enables requestors of urinary analysis services to be connected with providers of urinary analysis services via a software application ecosystem. Requestors may be in medical facilities lacking professionals with the skillset to review and analyze urinary test results. These may be in smaller or rural hospitals or labs, for example. A urinary analysis service provider, such as a nephrologist, is enabled to connect with a requestor via the application ecosystem via a network. The method includes a first step of detecting a request application executing on a computing device of a requestor, the request application automatically communicating with the service over a network. The method includes a second step of determining an availability of one or more available urinary analysis providers. The method includes a third step of providing data to the request application executing on the computing device to generate a presentation on a display of the computing device of the requestor, the presentation providing a user interface feature from which the requestor can trigger transmission of the service request to initiate, by the one or more servers, a selection process to assign the urinary analysis service request to one of the one or more providers. The service request received by a provider includes or is accompanied by at least an image of urine microscopy sample of a patient analyzed by a system of augmented intelligence. The said system of augmented intelligence comprises the steps of (i) receiving an image of urine microscopy sample of a patient, (ii) detecting a microscope light and a magnification technique used to take said image, (iii) classifying said image according to the presence of urinary sediments by a trained machine learning model, (iv) identifying sediments in said image with bounding boxes by said trained machine learning model if urinary sediments are present in said image in step (iii), (v) classifying said urinary sediments within said bounding boxes by said trained machine learning model, and (vi) generating a report of a presence or an absence of clinically significant urinary sediments in said urine microscopy sample from a predetermined list of clinically significant urinary sediments. The method includes a fifth step of in response to receiving the triggered transmission of the service request from the requestor interface feature, initiating the selection process by programmatically selecting an available provider from the one or more providers to be assigned to service for the requestor, and then providing information regarding the service request to the provider application executing on the computing device of the selected provider. The method includes a sixth step of upon the provider receiving the service request, the provider fulfills the service request, wherein said service request is fulfilled by the provider by reviewing said image of urine microscopy sample of said patient and verifying said report for accuracy.

In an exemplary workflow of the above computer-implemented method for operating one or more servers to provide a urinary analysis service, a physician who is a general practitioner may be staffing a rural emergency room. Due to its small nature, the rural emergency room would not have a staff nephrologist available to immediately review lab results for a patient with a urinary issue. The doctor can order a urine sample to be tested by the hospital's lab and the image will be returned. The image may be loaded into the application of the present invention and the doctor will request urinary analysis service, which may be performed remotely by a nephrologist who is using the application as a provider. The urine sample may be uploaded into the application, analyzed by the machine learning model to determine the microscope light and a magnification technique used to take the image, classify the image according to the presence of urinary sediments by a trained machine learning model, identify sediments in the image with bounding boxes by the trained machine learning model if urinary sediments are present in the image, classifying the urinary sediments within the bounding boxes by the trained machine learning model, and, optionally, generate a report of a presence or an absence of clinically significant urinary sediments in the urine microscopy sample from a predetermined list of clinically significant urinary sediments. The nephrologist can remotely review and verify the results and provide treatment plans back to the emergency room physician. The application may also include an ability for the parties to pay each other directly or for the provider to bill the patient's insurance company or the healthcare facility, for example, as appropriate.

In one embodiment, the software application has a user interface and operability for the provider to indicate whether the machine learning model correctly or incorrectly identified sediment or particles to further train the model.

Figure 20:
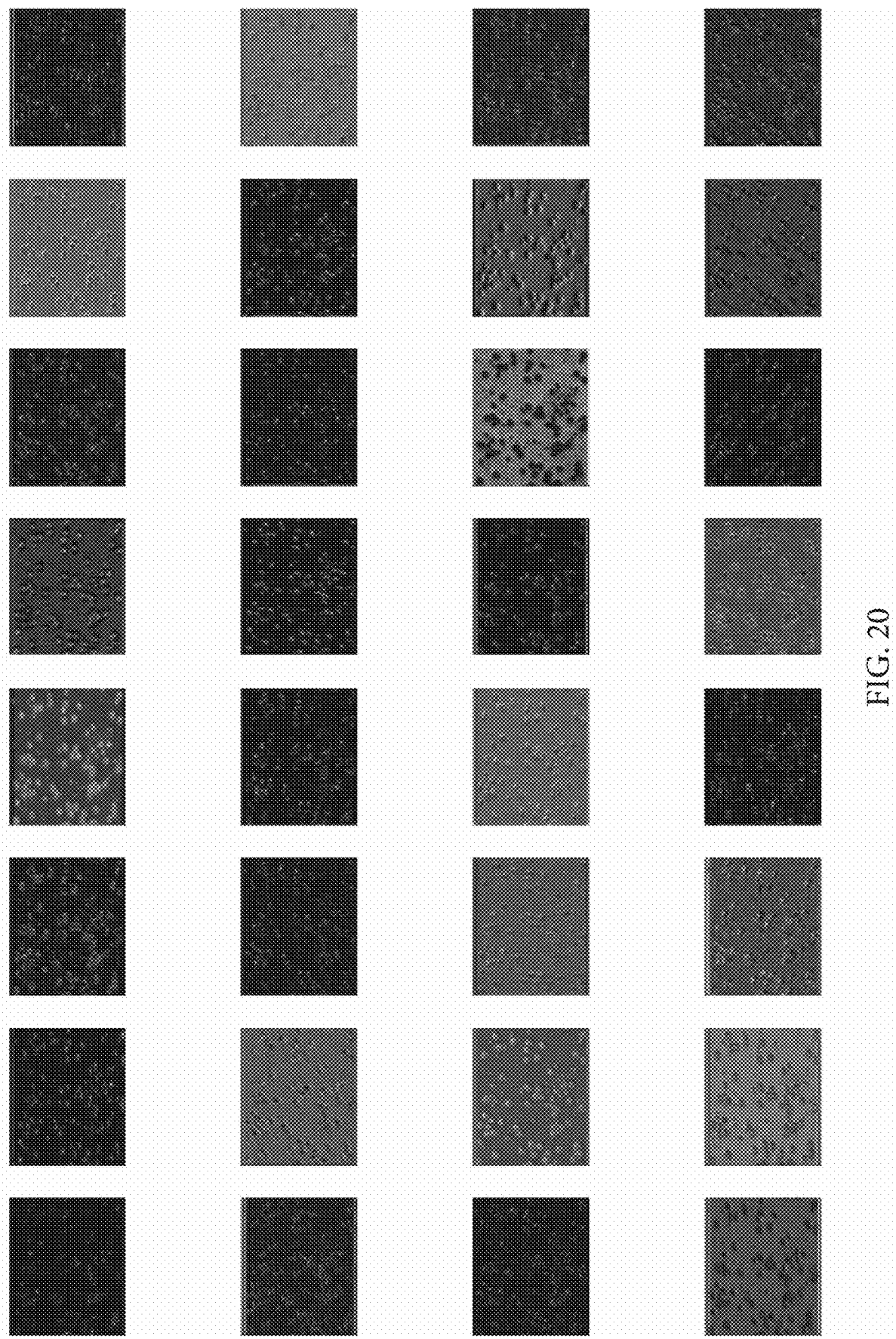
FIG. 20 depicts an example of Feature Visualization of the Machine Learning Model urinary analysis system in accordance with embodiments of the invention.

In some embodiments of the invention, the test results, image, notes, and any other data regarding a particular patient's sample may be stored on the server or transferred to an electronic medical records software system. Images captured as patient urine samples may also be used to train and refine machine learning models to improve accuracy. 'Feature visualization' as a means of model explainability and interpretability, which can assist in comprehending the models' predictions. The 'Feature visualization' provides clear and transparent explanations for the model's predictions; enables physicians to understand and validate the model's predictions; ensure that physicians can trust and justify the outcomes derived from the model; facilitate compliance with ethical and regulatory guidelines. One form of feature visualization is depicted in FIG. 20.

In some embodiments, the model includes "Ground Truth Generation" for computer vision and vision-language models.

Computer vision is utilized for the purposes of classification, detection, segmentation, and tracking.

In some embodiments, the model includes "Ground Truth Generation" for Vision-Language which utilizes Image-Text descriptions and Image-Label-Text annotations.

In some embodiments the report generated from the detections includes the use of standardized report information to create datasets to train other ML models. Once trained, these models can help generate reports. Therefore, the process is completely automated from sediment detection to report generation, wherein different task-specific models, one multimodal model, or a combination of both are utilized.

In some embodiments, models are deployed to generate simultaneous predictions and labels, creating an image-label dataset readable by other Machine Learning models. This enhances existing datasets and can be used for training new models or retraining existing models. One benefit of this process is the reduction of the economic burden of manual data labeling through task automation.

Instead of using separate models for predictions and annotation tasks, Machine Learning models can generate predictions and labels simultaneously. Processing an image through the model creates an image with annotations, resulting in an Machine Learning-readable dataset. The dataset can be used to enhance existing datasets or create new ones, which can be used for training or retraining models. This approach improves the efficiency of data labeling and contributes to the overall development and improvement of AI models.

Figure 17:
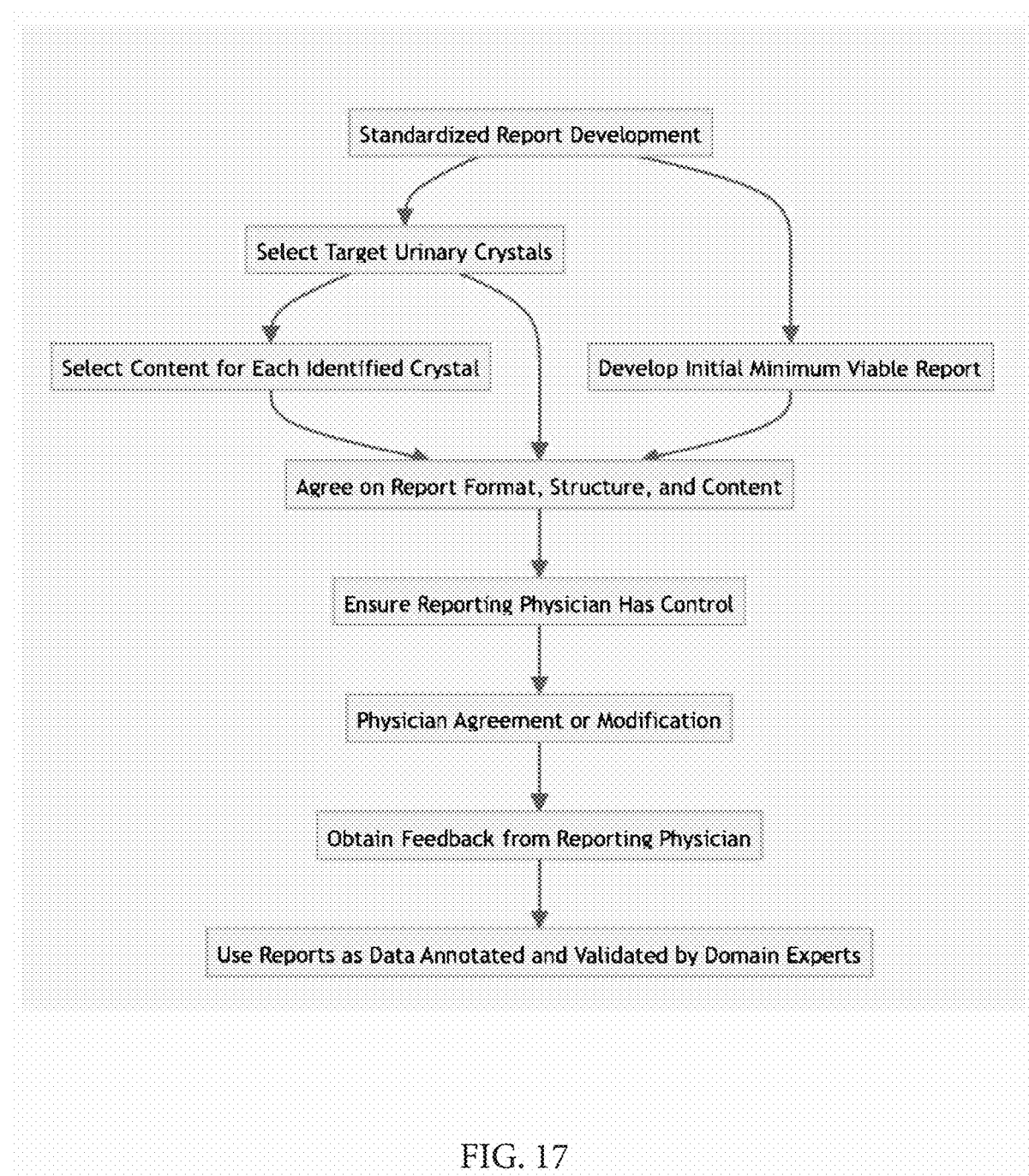
FIG. 17 depicts a method of developing a standardized report format in accordance with embodiments of the invention.
Figure 18:
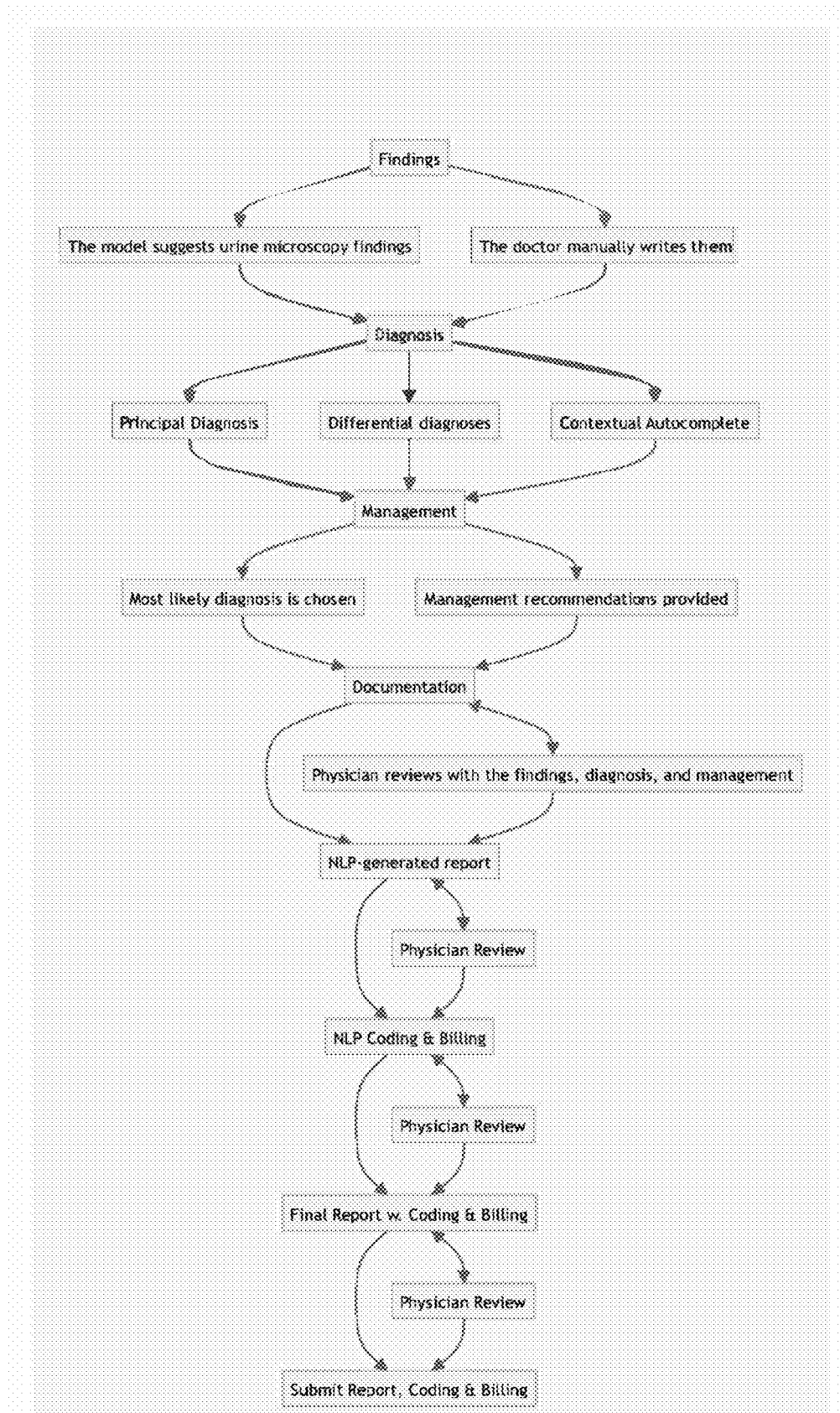
FIG. 18 depicts an improved physician workflow incorporating Machine Learning Model urinary analysis system and method in accordance with embodiments of the invention.

In some embodiments, a system of Standardized Report Development may be used to ensure the generation of Machine Learning digestible data while iteratively improving standard NLP tool performance. An example of this process is detailed in FIG. 17. A standardized report may be developed by domain experts and stakeholders to produce an initial minimum viable report.

The standardized report may be developed by the selection of target urinary crystals that are to be identified and reported; conditions that can benefit from early diagnosis and management (e.g., prevent complications, conditions with high morbidity and mortality). The reports may further me developed by the selection of the standardized content that will be generated for each identified sediment, such as: the disease associated with the identified sediment, the classes and/or quantity of identified sediments per image.

Reports can be developed based on the format, structure and content. For example, reports may use multiple-choice and pre-generated sentence options to populate the report content, standardized wording and vocabulary or anything affecting how the report is presented and the information explained to the physician.

Regardless of the standardized format, the reporting physician has the complete control and final decision on the report. The standardized reports may include a method for the physician to agree or disagree with the generated report; a method to modify the generated report; and a method to obtain feedback from the reporting physician.

The reports may be used as data annotated and validated by domain experts.

Figure 16:
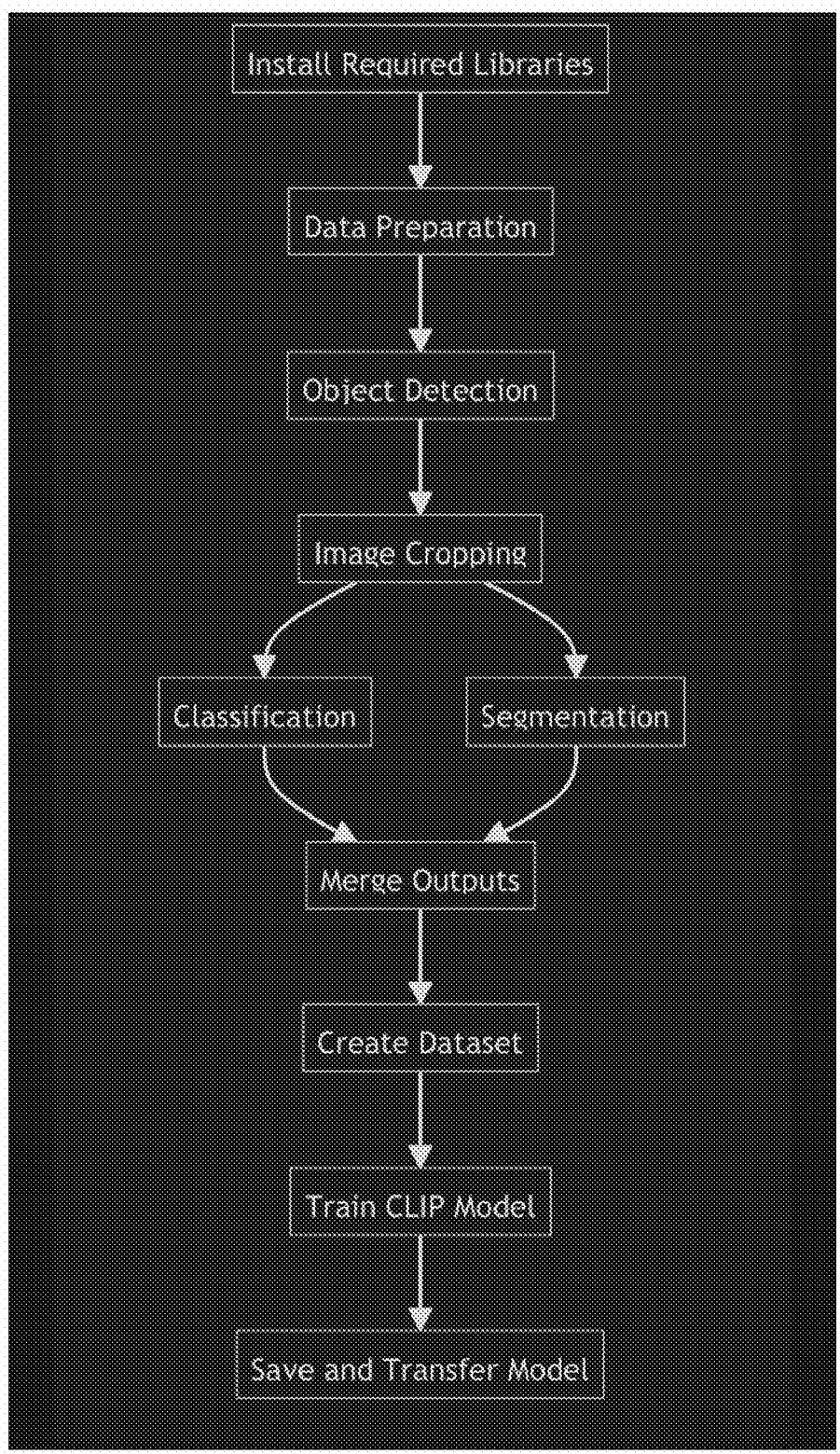
FIG. 16 depicts a method of training a Machine Learning Model in accordance with embodiments of the invention.

In some embodiments the model utilizes Multimodal Model Training. An example of a process of Multimodal Model Training is depicted in FIG. 16.

Machine learning may create one or more training datasets from microscopic images and may create text-based dataset outputs or any suitable form of dataset.

The model can be used at different institutions such as research institutions, hospitals, clinics, etc. Laboratory and clinical data from local populations and healthcare scenarios can be added.

The standardized reports may be used to train NLP models to generate reports automatically.

Feedback from reporting physicians may be used to fine-tune the model and train new custom models or re-train older models.

Feedback may be positive; in that it is added to training data.

In some embodiments the feedback may be in the form of physician modified reports. The Machine Learning model may analyze modified content and consider adding modified reports to training data. This may be used such that Machine Learning Model begins to modify its own report format to suit individual or large-scale preferences.

Feedback may be in the form of negative reports. Poorly reviewed, flagged, or incorrect reports may be removed from training data. ML Models may analyze report content, degree of failure, and cause of failure.

ML Models may identify the areas of the report and the specific content that caused the physician to disagree with it and seek to avoid those conditions in the future.

In some embodiments, the ML Model may utilize a method of real time comparison with the Physicians manual analysis and reporting. For example, the ML Model may, while a physician is doing his regular workflow, operate in the background, and use the same data as the physician to generate its own analysis and report. The model then compares its performance against the physician's. This method can be used at different workflow levels, including sediment detection, classification, report generation, etc.

In some embodiments the model utilizes background inference, Deployment & Simultaneous Live A/B Test. A nephrologist or domain expert may process new live patient data or use a previously trained ML model. The previously trained model is simultaneously deployed in the background while the new model operates. The new model is tested on the same live patient data. A nephrologist, domain expert or different AI or ML model evaluates and compares the performances of the old and new models using predefined evaluation metrics. This helps avoid the risks of deploying a less accurate and/or underperforming model and may help reduce the learning curve.

A nephrologist, domain expert or different AI or ML mode may consider deploying the new model if all of the following criteria are met: Computer Testing: The new model achieves equal or better performance than the old model based on predetermined evaluation metrics on validation and testing datasets. For example, the new model's accuracy exceeds that of the old model by a predetermined value in both the validation and testing datasets. Live Testing: The new model outperforms the old model by a predetermined value in live testing, as measured by predefined metrics and a composite score. No patient harm: The model performance does not indicate the risk of patient harm. Committee Approval: Domain experts and stakeholders agree to proceed with the deployment.

Figure 19:
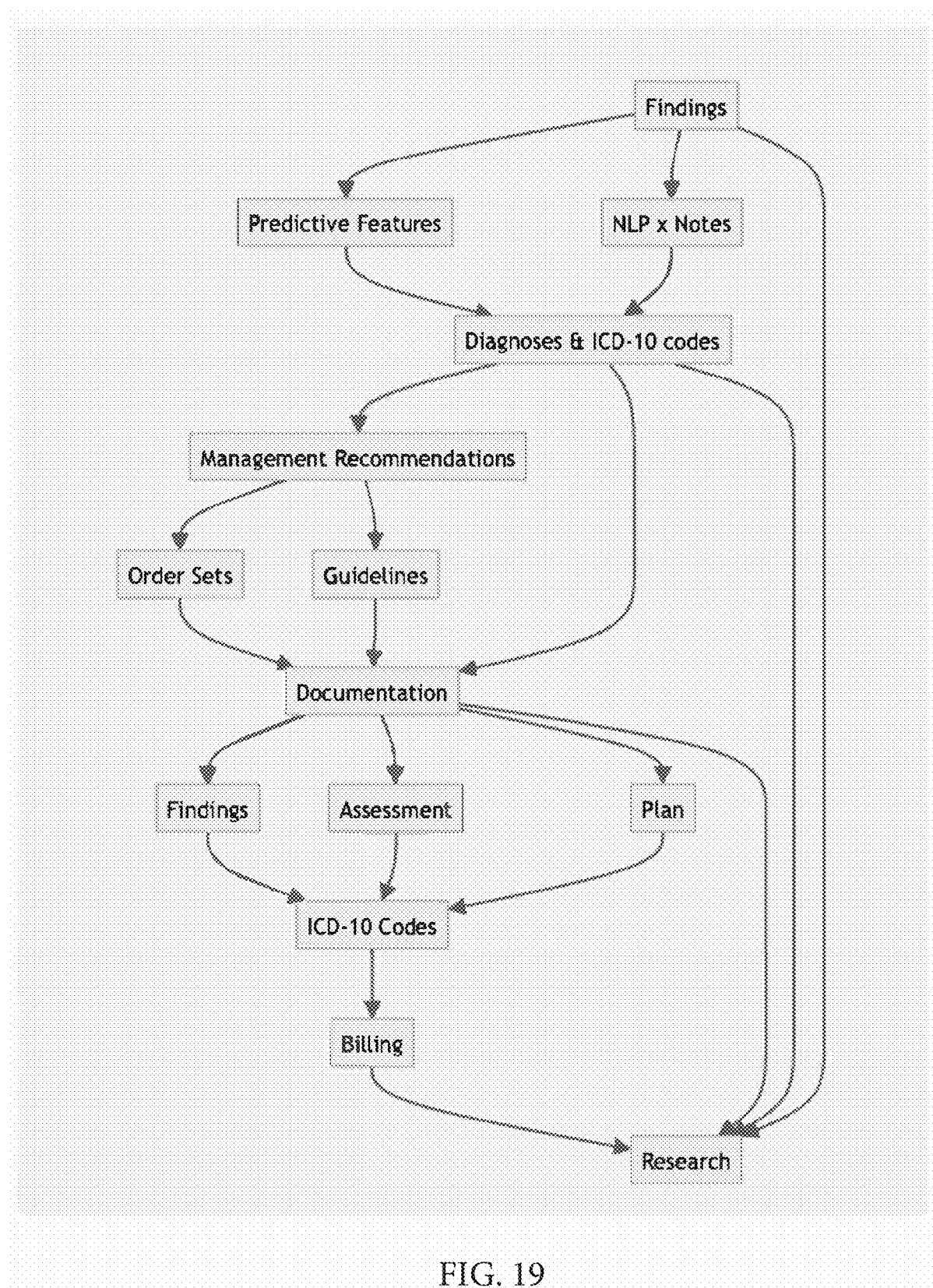
FIG. 19 depicts a chart of the potential healthcare processes that may be integrated with the urinary analysis system and method in accordance with embodiments of the invention.

In some embodiments, the healthcare processes can be integrated with the Augmented Urinalysis to implement an augmented clinical decision support system. A non-exhaustive chart of some of the processes that may be integrated is depicted in FIG. 19. FIG. 19 illustrates an implementation of the invention's features to contribute to the predictive modeling to optimize current workflows and resource allocation. Some examples of potentially integrated processes are: Findings (the model may suggests urine microscopy findings, or the doctor manually writes them) and Predictive Features, such as Demographic Data, Past Medical History data, Progress Notes data, and additional clinical and demographic data.

Additional processes that may be integrated are: Coding: Diagnosis w/ICD-10 codes including Principal and Differential diagnoses, ICD-10 Codes; Diagnosis Review such as results Reviewed and Selected by Physician; Recommendations for the selected diagnoses; Order Sets; Guidelines; Management Review (where the physician agrees with the findings, diagnosis, and management. Results can be sent to remote physicians for review.); Documentation (NLP-generated reports such as Standardized Findings Documentation, Assessment, Final Diagnosis and ICD-10 codes, Plan/Recommendations); Documentation Review; Billing (Autogenerated ICD-10 codes recommendations based on: Documentation, ICD-10 codes); Review Codes and Submit Billing; Research (Structured Predictive Features, Documentation, Billing)

The implementation of AI will likely change the workflow and responsibilities of healthcare professionals involved in urine analysis. With ML handling the analysis of urine samples, healthcare professionals can focus more on interpreting the results, making treatment decisions, and providing personalized care to patients.

Physician role can shift from performing repetitive and time-consuming tasks to leveraging the insights provided by the ML application for more effective patient management.

The integration of AI into urine analysis has the potential to impact patient outcomes and healthcare quality positively ML can enhance the accuracy and efficiency of urine analysis, leading to faster and more accurate diagnoses. The timely detection of pathologic sediments can enable early interventions and personalized treatment plans, improving patient outcomes. Additionally, ML can assist healthcare professionals in making informed decisions, reducing errors, and enhancing overall healthcare quality. For the purposes of promoting an understanding of the principles of the invention, reference has been made to the preferred embodiments illustrated in the drawings, and specific language has been used to describe these embodiments. However, this specific language intends no limitation of the scope of the invention, and the invention should be construed to encompass all embodiments that would normally occur to one of ordinary skill in the art. The particular implementations shown and described herein are illustrative examples of the invention and are not intended to otherwise limit the scope of the invention in any way. For the sake of brevity, conventional aspects of the system (and components of the individual operating components of the system) may not be described in detail. Furthermore, the connecting lines, or connectors shown in the various figures presented are intended to represent exemplary functional relationships and/or physical or logical couplings between the various elements. It should be noted that many alternative or additional functional relationships, physical connections or logical connections may be present in a practical device. Moreover, no item or component is essential to the practice of the invention unless the element is specifically described as "essential" or "critical". Numerous modifications and adaptations will be readily apparent to those skilled in this art without departing from the spirit and scope of the present invention.

What is claimed is:

1. A computer-implemented method for performing urinary analysis implemented on one or more processors and associated memory, comprising:
   (a) receiving an image of urine microscopy sample of a patient;
   (b) detecting a microscope light and a magnification technique used to take said image;
   (c) classifying said image according to the presence of urinary sediments by a trained machine learning model;
   (d) identifying urinary sediments by said trained machine learning model if urinary sediments are present in said image in step (b);
   (e) classifying said urinary sediments by said trained machine learning model; and
   (f) generating a report of a presence or an absence of clinically significant urinary sediments in said urine microscopy sample from a predetermined list of clinically significant urinary sediments.

2. The computer-implemented method of claim 1, wherein said machine learning model identified and classifies said urinary sediments with bounding boxes or segmentation masks.

3. The computer-implemented method of claim 1, wherein said sediments are casts, acanthocytes, or crystals.

4. The computer-implemented method of claim 1, further comprising the step of diagnosing, by said trained machine learning model, a condition of said patient.

5. The computer-implemented method of claim 1, further comprising the step of recommending, by said trained machine learning model, a treatment plan for said patient.

6. The computer-implemented method of claim 1, further comprising the step of accounting for variation in microscope light and a magnification technique used to take said image between steps (b) and (c).

7. A computer-implemented method for operating one or more servers to provide a urinary analysis service, the method comprising:
   (a) detecting a request application executing on a computing device of a requestor, the request application automatically communicating with the service over a network;
   (b) determining an availability of one or more available urinary analysis providers available to review an image a urine microscopy sample of a patient;
   (c) providing data to the request application executing on the computing device to generate a presentation on a display of the computing device of the requestor, the presentation providing a user interface feature from which the requestor can trigger transmission of the service request to initiate, by the one or more servers, a selection process to assign the urinary analysis service request to one of the one or more providers;
   (d) wherein the service request received by a provider includes or is accompanied by at least an image of urine microscopy sample of a patient analyzed by a system of augmented intelligence, said system comprising:
      (i) receiving an image of urine microscopy sample of a patient;
      (ii) detecting a microscope light and a magnification technique used to take said image;
      (iii) classifying said image according to the presence of urinary sediments by a trained machine learning model;
      (iv) identifying sediments in said image by said trained machine learning model if urinary sediments are present in said image in step (iii);
      (v) classifying said urinary sediments by said trained machine learning model; and
      (vi) generating a report of a presence or an absence of clinically significant urinary sediments in said urine microscopy sample from a predetermined list of clinically significant urinary sediments;
   (e) in response to receiving the triggered transmission of the service request from the requestor interface feature, initiating the selection process by programmatically selecting an available provider from the one or more providers to be assigned to service for the requestor, and then providing information regarding the service request to the provider application executing on the computing device of the selected provider; and
   (f) upon the provider receiving the service request, the provider fulfills the service request, wherein said service request is fulfilled by the provider by reviewing said image of urine microscopy sample of said patient, verifying said report for accuracy or providing corrections, and transmitting said verification, said correction, and said treatment plans to said requestor.

8. The computer-implemented method of claim 7, wherein said machine learning model identified and classifies said urinary sediments with bounding boxes or segmentation masks.

9. The computer-implemented method of claim 7, further comprising the step of detecting a microscope light and a magnification technique used to take said image.

10. The computer-implemented method of claim 7, further comprising the step of diagnosing, by said trained machine learning model, a condition of said patient.

11. The computer-implemented method of claim 7, wherein said software application is operable for said provider to indicate whether the machine learning model correctly or incorrectly identified sediment or particles to further train the model.

12. The computer-implemented method of claim 7, further comprising the step of recommending, by said trained machine learning model, a treatment plan for said patient.

13. The computer-implemented method of claim 7, wherein said sediments are casts, acanthocytes, or crystals.

14. A computer-implemented method for operating one or more servers to provide a urinary analysis service, the method comprising:
   (a) detecting a request application executing on a computing device of a requestor, the request application automatically communicating with the service over a network;
   (b) determining an availability of one or more available urinary analysis providers available to review an image a urine microscopy sample of a patient;
   (c) providing data to the request application executing on the computing device to generate a presentation on a display of the computing device of the requestor, the presentation providing a user interface feature from which the requestor can trigger transmission of the service request to initiate, by the one or more servers, a selection process to assign the urinary analysis service request to one of the one or more providers;
   (d) wherein the service request received by a provider includes or is accompanied by at least an image of urine microscopy sample of a patient analyzed by a system of augmented intelligence, said system comprising:

receiving an image of urine microscopy sample of a patient; and identifying a presence or an absence of clinically significant urinary sediments in said urine microscopy sample;

(e) in response to receiving the triggered transmission of the service request from the requestor interface feature, initiating the selection process by programmatically selecting an available provider from the one or more providers to be assigned to service for the requestor, and then providing information regarding the service request to the provider application executing on the computing device of the selected provider; and (f) upon the provider receiving the service request, the provider fulfills the service request, wherein said service request is fulfilled by the provider by reviewing said image of urine microscopy sample of said patient and said identification of said presence or said absence of clinically significant urinary sediments in said urine microscopy sample, and wherein said provider transmits results of said review to said requestor.

15. The computer-implemented method of claim 14, further comprising detection of a microscope light and a magnification technique used to take said image.

16. The computer-implemented method of claim 14, further comprising generating a report of a presence or an absence of clinically significant urinary sediments in said urine microscopy sample from a predetermined list of clinically significant urinary sediments.

17. The computer-implemented method of claim 14, further comprising the step of diagnosing, by said trained machine learning model, a condition of said patient.

18. The computer-implemented method of claim 14, further comprising the step of recommending, by said trained machine learning model, a treatment plan for said patient.

19. The computer-implemented method of claim 14, wherein said sediments are casts, acanthocytes, or crystals.

* * * * *